(12) United States Patent
Macsovits

(10) Patent No.: US 8,778,004 B2
(45) Date of Patent: Jul. 15, 2014

(54) THERAPEUTIC DEVICE

(76) Inventor: Rebecca Wilson Macsovits, Englewood, CO (US)

( * ) Notice: Subject to any disclaimer, the term of this patent is extended or adjusted under 35 U.S.C. 154(b) by 0 days.

(21) Appl. No.: 13/571,206

(22) Filed: Aug. 9, 2012

(65) Prior Publication Data
US 2013/0041435 A1 Feb. 14, 2013

Related U.S. Application Data

(63) Continuation of application No. 12/365,264, filed on Feb. 4, 2009, now Pat. No. 8,262,631.

(51) Int. Cl.
*A61F 7/00* (2006.01)

(52) U.S. Cl.
USPC .................. 607/96; 601/47; 601/57

(58) Field of Classification Search
None
See application file for complete search history.

(56) References Cited

U.S. PATENT DOCUMENTS

| | | | |
|---|---|---|---|
| 3,062,203 A | 11/1962 | Ziff | |
| 3,664,332 A | 5/1972 | Vecchio | |
| 4,335,725 A | 6/1982 | Geldmacher | |
| 4,607,624 A | 8/1986 | Jefferson | |
| 4,979,502 A | 12/1990 | Hunt | |
| 5,902,256 A * | 5/1999 | Benaron | 601/15 |
| 6,142,963 A * | 11/2000 | Black et al. | 601/57 |
| 7,147,610 B2 | 12/2006 | Maalouf | |
| 7,182,739 B2 | 2/2007 | Kopanic et al. | |
| 8,262,631 B1 | 9/2012 | Macsovits | |
| 2003/0131416 A1* | 7/2003 | Lee | 5/652 |
| 2007/0142891 A1* | 6/2007 | Stanley | 607/144 |
| 2009/0304217 A1 | 12/2009 | Thalheimer et al. | |
| 2010/0262050 A1* | 10/2010 | Gasparovich | 601/57 |

OTHER PUBLICATIONS

"Conair Model HP08 Massaging Heating Pad," The Unwind.company, dated Nov. 2007, found at http://web.archive.org/web/s0071107160652/http://www.unwind.com/Merchant2/merchant.mvc?Screen=PROD&Product_Code, 3 pages.
"Heat Therapy Air Activated Heat Pads With Back Wrap," Healiohealth, dated May 2008, found at http://web.archive.org/web/20080517232956/http://www.healiohealth.com/tek9.asp?pg=products&specific=jrnqdnp4, 4 pages.
"Pain Relief Without Medicine," Caregiver Resources, Oct. 2006, found at http://web.archive.org/web/20061016085016/http://www.caregiverslibrary.org/Default.aspx?tabid=312, 4 pages.

(Continued)

*Primary Examiner* — Leslie Deak
*Assistant Examiner* — Sara Sass
(74) *Attorney, Agent, or Firm* — Sheridan Ross P.C.

(57) ABSTRACT

A therapeutic device includes an elastomeric outer shell configured as a human hand and defining an interior area, the outer shell having a finger end opposite a wrist end. The device includes a pocket in the interior area, the pocket being defined by an inner wall. An endplate is coupled to the outer shell and coupled to the inner wall to define a closed area between the outer shell and pocket, the endplate having an opening for allowing access to the pocket. A fill material is positioned in the closed area. The device includes a vibrating unit removably positioned in the pocket through the endplate opening, the vibrating unit having a lock complementary to a catch to couple the vibrating unit to the endplate, the vibrating unit having a vibrating motor in electrical communication with a power source and a switch.

11 Claims, 8 Drawing Sheets

(56) References Cited

OTHER PUBLICATIONS

Lorzadeh et al. "Smart Massage Patch," Canadian Conference on Electrical and Computer Engineering, 2007, CCECE 2007, Apr. 2007, pp. 210-213.

Official Action for U.S. Appl. No. 12/365,264, mailed Aug. 8, 2011, Restriction Requirement.
Notice of Allowance for U.S. Appl. No. 12/365,264, mailed May 11, 2012.
Official Action for U.S. Appl. No. 12/365,264, mailed Feb. 21, 2012.

* cited by examiner

THERAPEUTIC DEVICE

CROSS-REFERENCE TO RELATED APPLICATION

This application is a continuation of U.S. patent application Ser. No. 12/365,264 filed Feb. 4, 2009, and entitled "Therapeutic Device," now U.S. Pat. No. 8,262,631, the disclosure of which is incorporated herein by reference in its entirety.

BACKGROUND OF THE INVENTION

This invention relates generally to therapeutic devices and, more particularly, to a vibrating thermal therapy device that is useful to soothe and comfort an infant or other child who may be suffering from an upset or aching stomach.

One instance that often causes an infant, toddler, or even older child to fuss or be uncomfortable is an upset stomach. A parent or other caregiver may choose to soothe and comfort the fussy child by holding or rocking the child. Further, the caregiver may rub the child's stomach area with his hand, thereby providing soothing heat and vibration to the skin.

Various devices have been proposed in the art for enhancing the comfort of a fussy child. Although assumably effective for their intended purposes, the existing devices do not sufficiently or thoroughly emulate the benefits of a person's hand positioned or moving upon the skin of a child.

Therefore, it would be desirable to have a therapeutic device having a configuration that simulates both the appearance and feeling of a human hand. Further, it would be desirable to have a therapeutic device that provides heat to a child's stomach that is soothing to a child with an upset stomach. In addition, it would be desirable to have a therapeutic device that provides vibration and music that is comforting.

SUMMARY OF THE INVENTION

A therapeutic device according to the present invention includes an elastomeric outer shell configured as a human hand and defining an interior area, the outer shell having a finger end opposite a wrist end. The device includes a pocket in the interior area, the pocket being defined by at least one inner wall. An endplate is coupled to the outer shell at the wrist end and coupled to the at least one inner wall to define a closed area between the outer shell and the pocket, the endplate having an opening for allowing access to the pocket, the endplate defining a catch adjacent the opening. A fill material is situated in the closed area. The device includes a vibrating unit removably positioned in the pocket through the endplate opening, the vibrating unit having a lock complementary to the catch to selectively couple the vibrating unit to the endplate. The vibrating unit includes a vibrating motor in electrical communication with a power source and a switch, the switch being accessible when the vibrating unit is positioned in the pocket through the endplate opening.

Therefore, a general object of this invention is to provide a therapeutic device to soothe and comfort an infant with an upset stomach.

Another object of this invention is to provide a therapeutic device, as aforesaid, that emulates a human hand.

Still another object of this invention is to provide a therapeutic device, as aforesaid, that includes a fill material that is microwavable.

Yet another object of this invention is to provide a therapeutic device, as aforesaid, that includes a vibration device that selectively vibrates the therapeutic device.

A further object of this invention is to provide a therapeutic device, as aforesaid, that includes a music device.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 3b is an isolated view on an enlarged scale taken from FIG. 3a;

DESCRIPTION OF THE PREFERRED EMBODIMENT

A therapeutic device will now be described in detail with reference to FIG. 1 through FIG. 8 of the accompanying drawings. More particularly, a therapeutic device 100 includes an outer shell 110, an endplate 120, and fill material 130.

Figure 1:
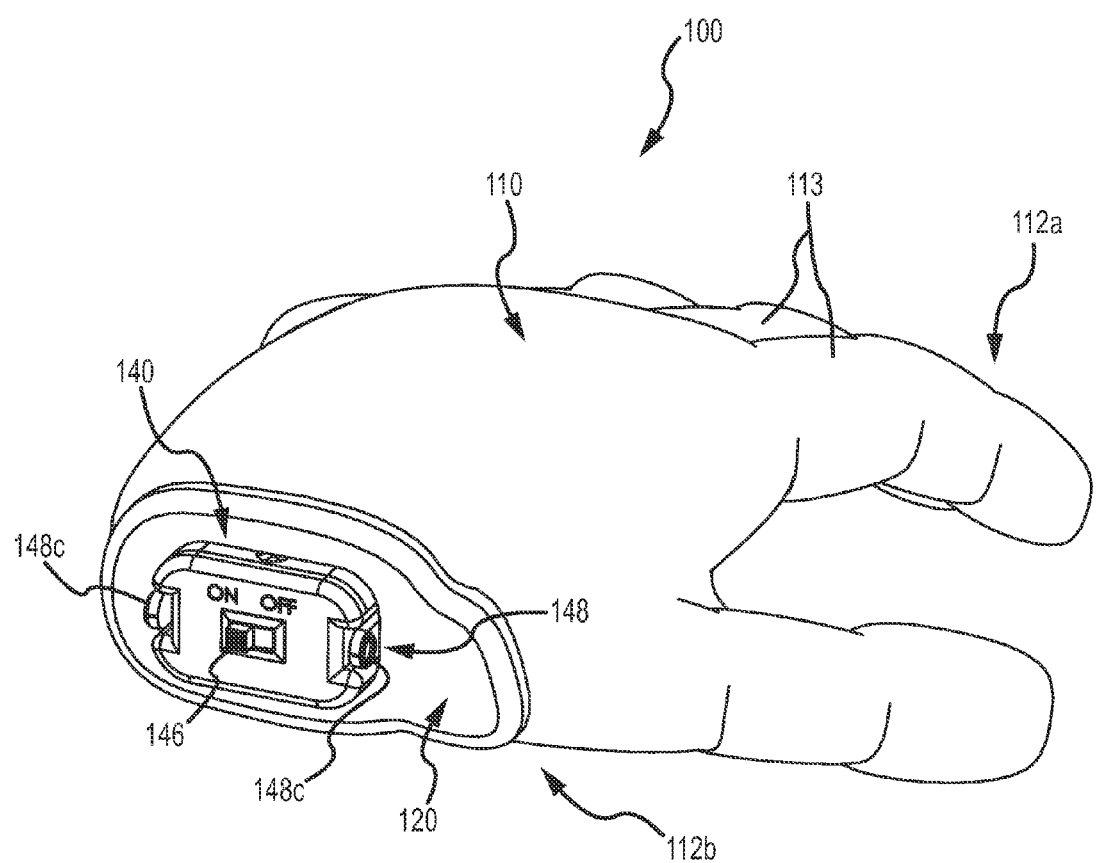
FIG. 1 is a perspective view of a therapeutic device according to a preferred embodiment of the present invention.
Figure 2:
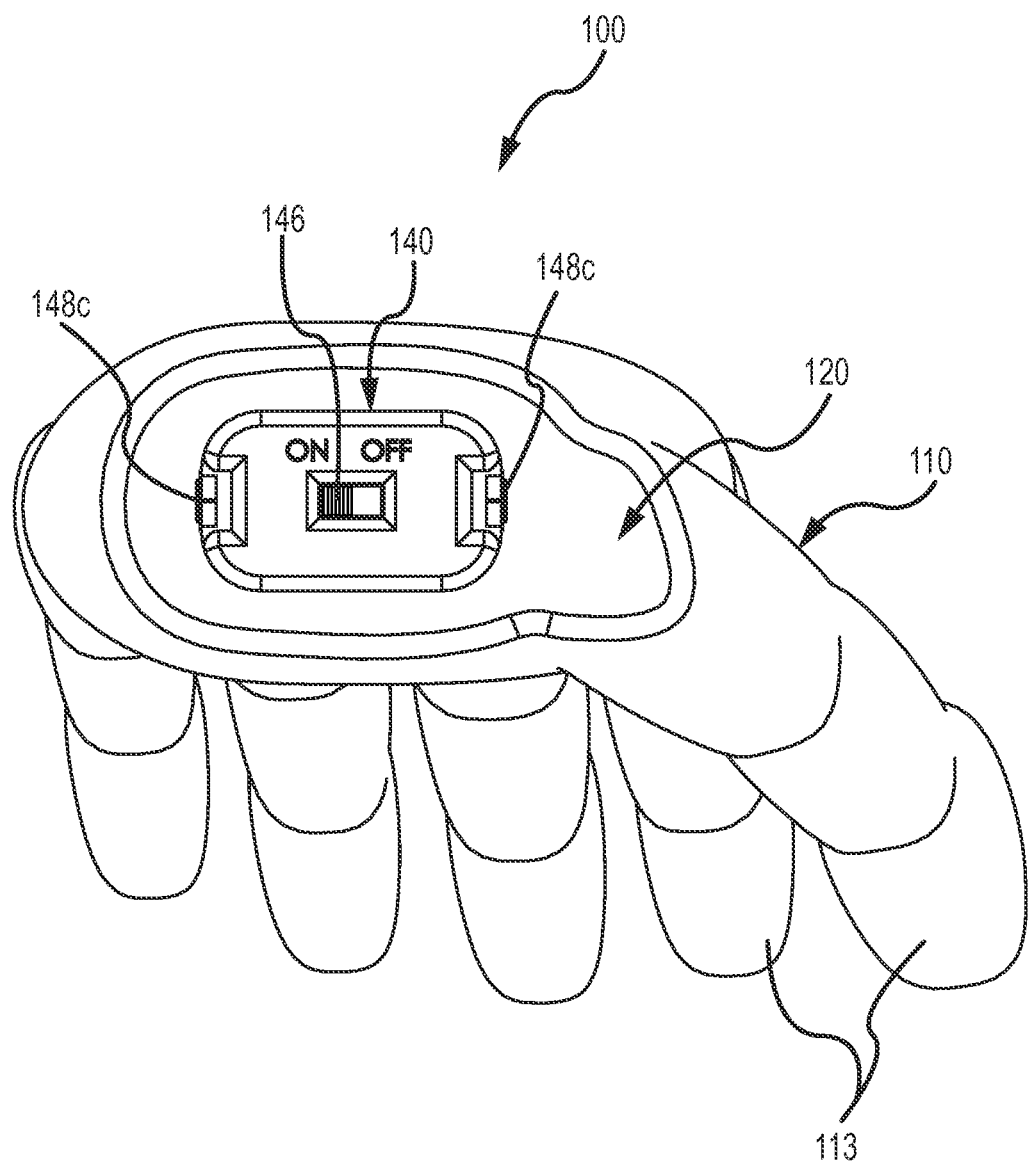
FIG. 2 is a rear view of the therapeutic device as in FIG. 1.
Figure 7:
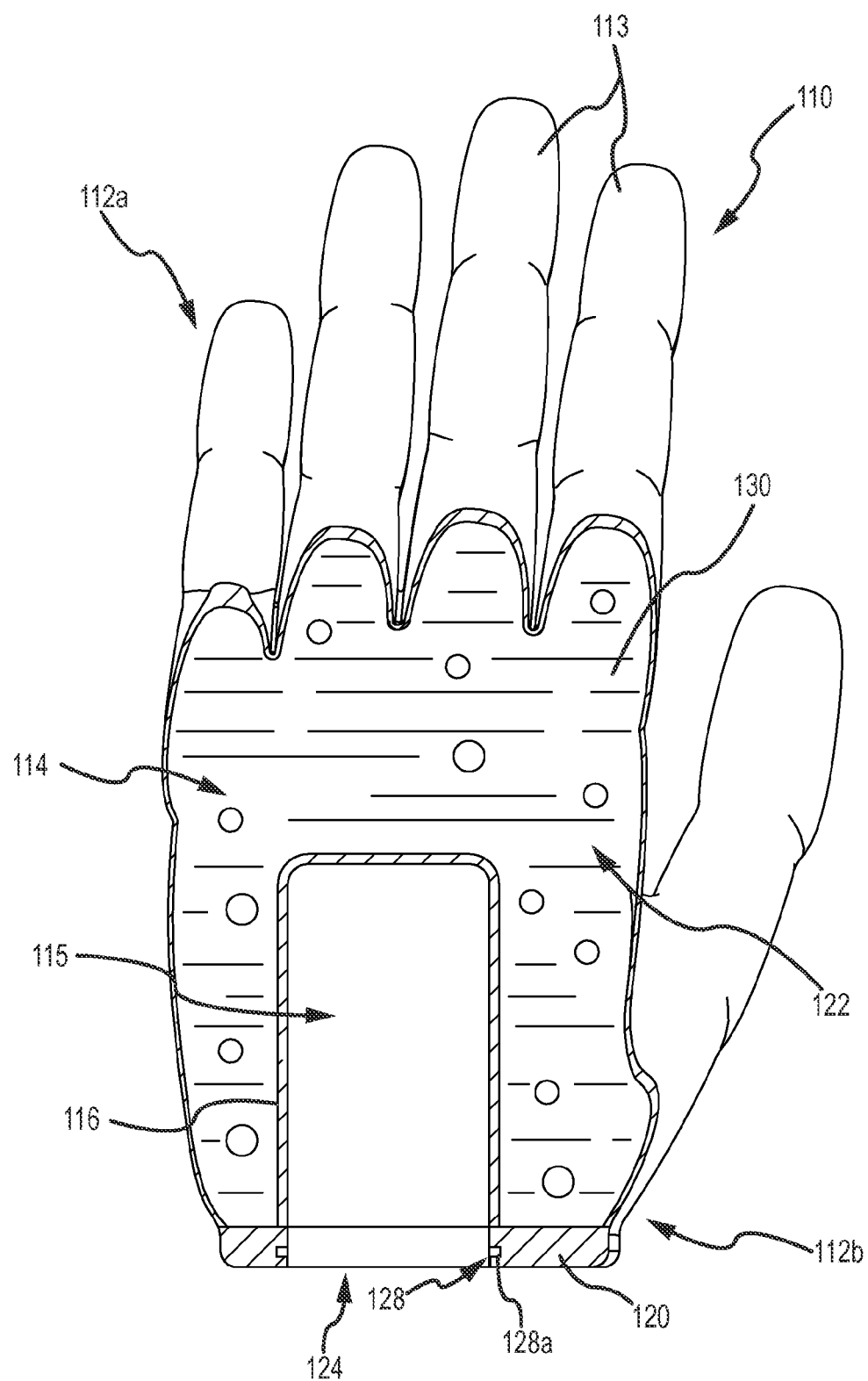
FIG. 7 is a cross-sectional view taken along line 7-7 of FIG. 6.

As shown in FIGS. 1 and 7, the outer shell 110 is configured as a human hand (i.e., includes fingers 113 at a finger end 112a that is opposite a wrist end 112b) and defines an interior area 114. A pocket 115 (FIGS. 6 and 7) is in the interior area 114 and is defined by at least one inner wall 116. In some embodiments, the outer shell 110 is elastomeric to allow movement of the hand (e.g., the fingers 113).

The endplate 120 is coupled to the outer shell 110 at the wrist end 112b through adhesion, fusion, or any other appropriate method, and coupled to the inner wall(s) 116 through adhesion, fusion, or any other appropriate method, to define a closed area 122 between the outer shell 110 and the pocket 115, as shown in FIGS. 1 and 7. In some embodiments, the outer shell 110, endplate 120, inner wall(s) 116, and seams between those elements are generally impermeable so that the closed area 122 is generally impermeable. The endplate 120 may be rigid and has an opening 124 (FIGS. 6 and 7) for allowing access to the pocket 115.

FIG. 7 shows that the fill material 130 may be located in the closed area 122. The fill material 130 may be microwavable to provide therapeutic heat and refrigeratable to provide therapeutic chill. In other words, the fill material 130 may be constructed of a material that can alternately become hot and cold (e.g., through microwave energy, placement in a freezer, etc.) and that can maintain the desired temperature for extended periods of time. Such materials are known in the art, and include gels, liquids, and pellets, for example. One appropriate fill material 130 is commonly known and sold as Techni Ice, marketed by Techni Ice Australia. While it may be advantageous for many fill materials 130 to have an impermeable closed area 122 as set forth above, other fill materials 130

(e.g., Techni Ice) may benefit from permeable material(s) that allow the fill material 130 to hydrate or otherwise interact with substances outside the closed area 122.

To allow the fill material 130 to be heated and cooled, the outer shell 110, inner wall(s) 116, and endplate 120 may be constructed of materials that are microwave and freezer safe. As such, these elements may be heated and cooled along with the fill material 130. In some embodiments, the outer shell 110 and the inner wall(s) 116 are constructed of the same material.

Figure 3A:
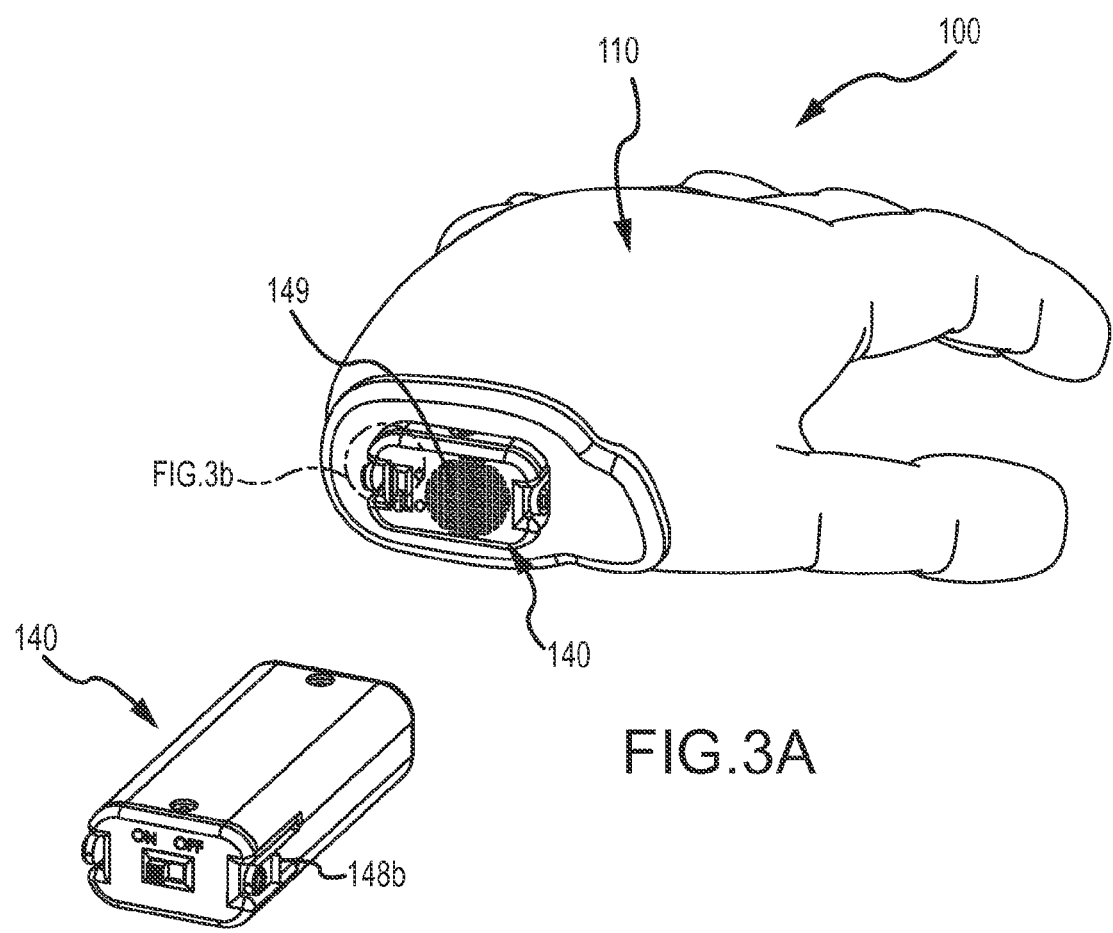
FIG. 3a is an exploded view of the therapeutic device as in FIG. 1.
Figure 4:
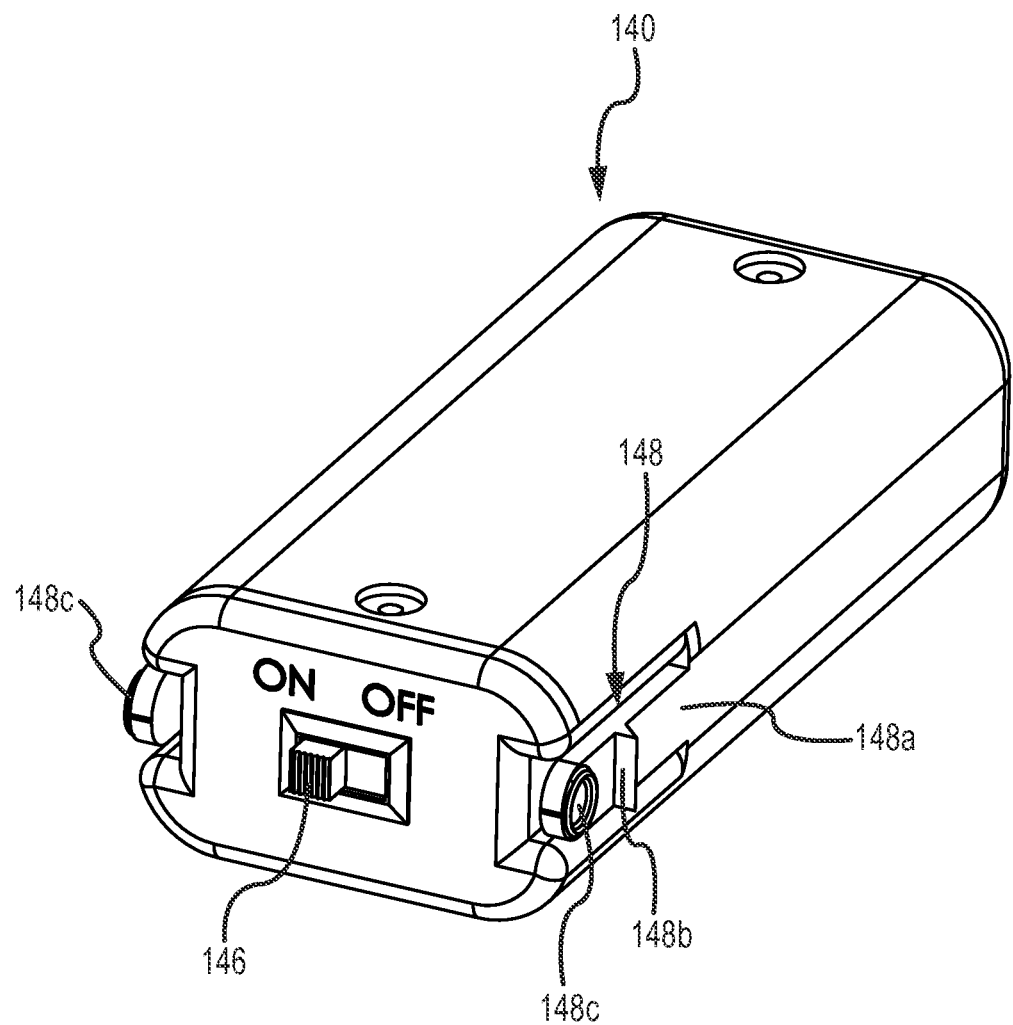
FIG. 4 is a perspective view on an enlarged scale of the enhancing unit according to the present invention.
Figure 5:
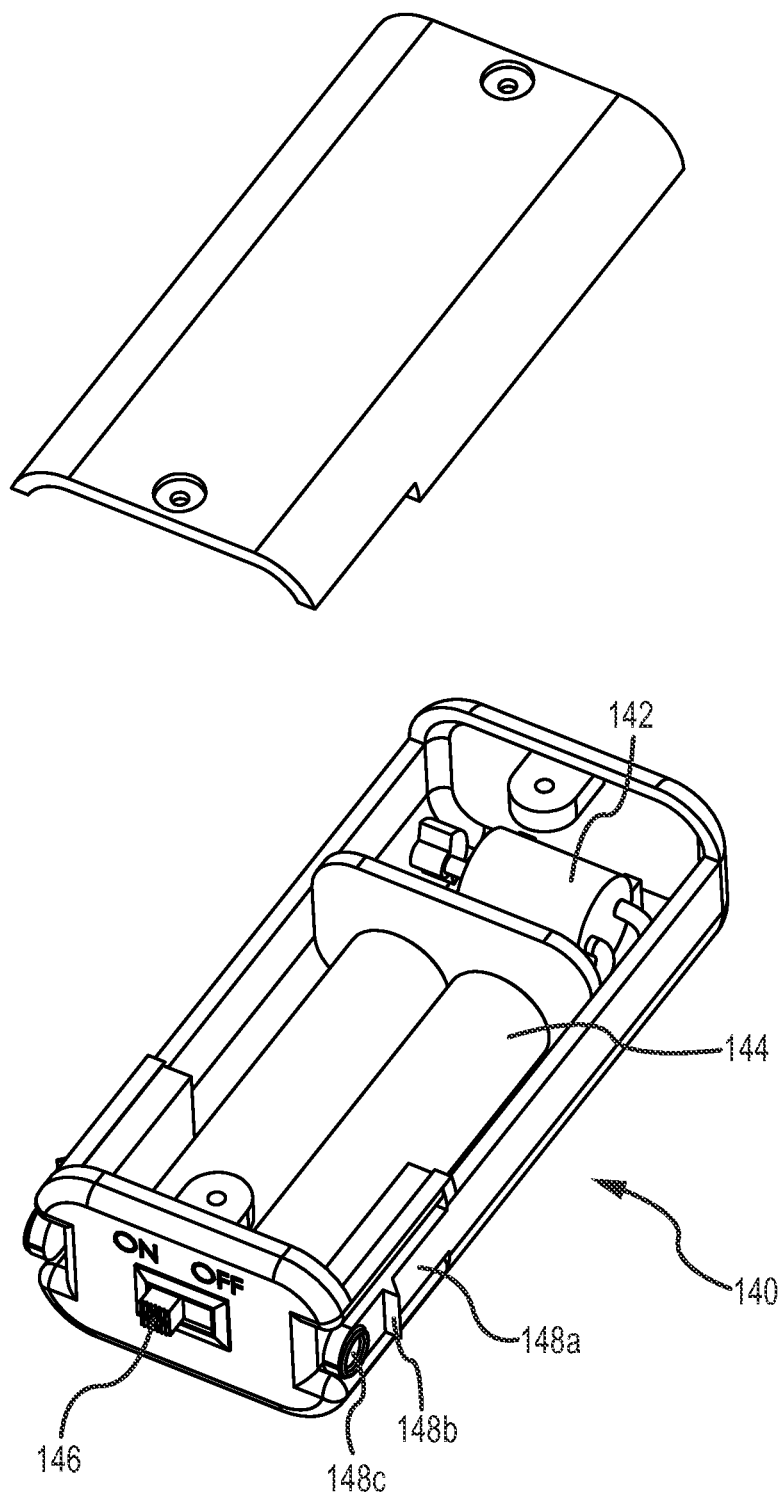
FIG. 5 is an exploded view of the enhancing unit as in FIG. 4.
Figure 6:
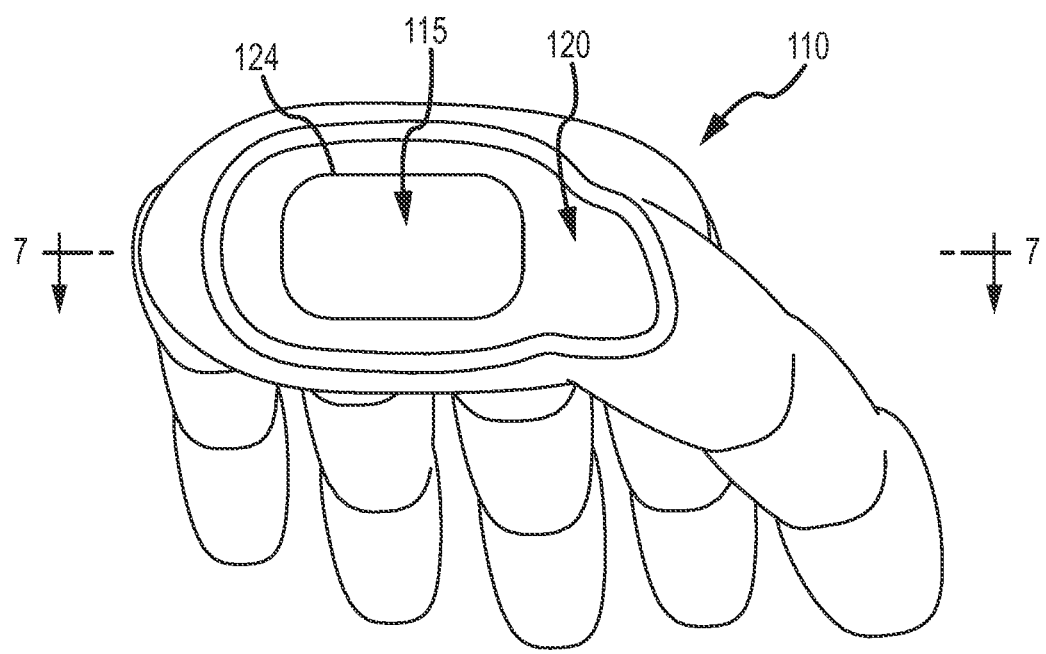
FIG. 6 is a rear view of the therapeutic device with the enhancing unit removed.
Figure 8:
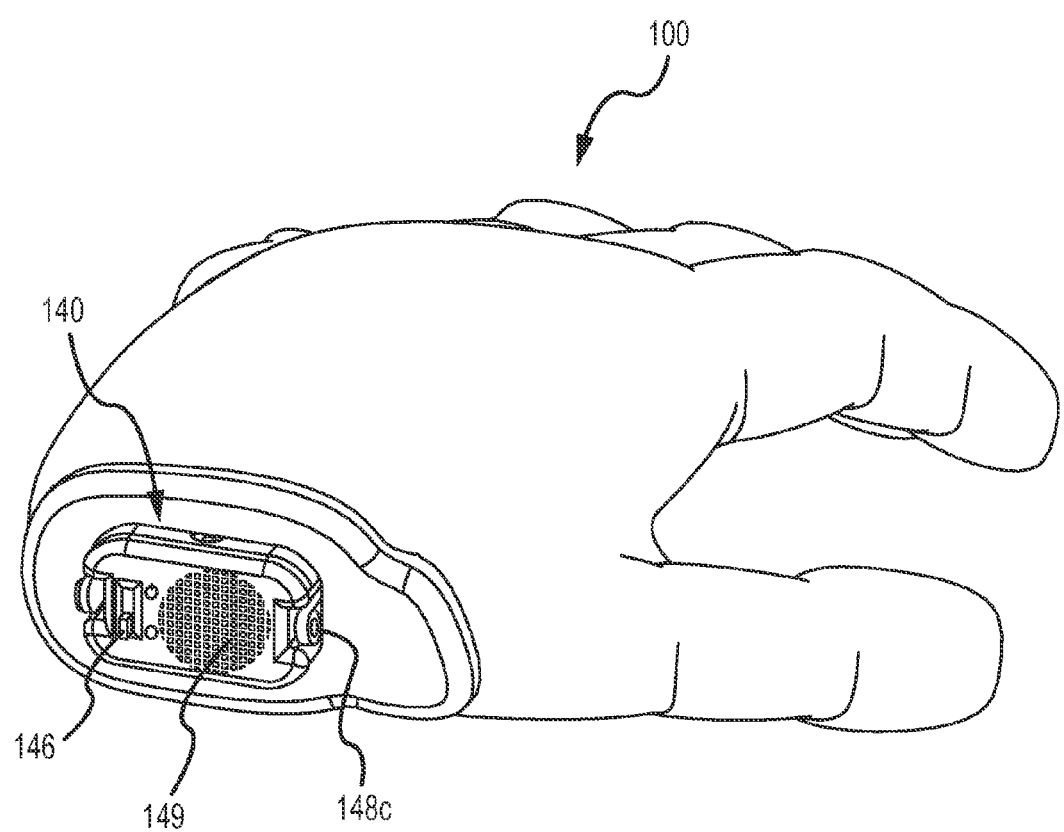
FIG. 8 is a rear perspective showing that the enhancing unit may include a speaker.

At least one enhancing unit 140 (FIGS. 1 through 5 and 8) may be removably positioned in the pocket 115 through the endplate opening 124 to provide an audible, visual, and/or tactile effect (e.g., a vibration). For example, as shown in FIG. 5, the enhancing unit 140 may include a vibrating motor 142 in electrical communication with a power source 144 (e.g., a battery, etc.) and a switch 146 for actuating the motor 142. The switch may be accessible when the enhancing unit 140 (an enhancing unit 140 with a vibrating motor 142 may also be referred to herein as a "vibrating unit") is positioned in the pocket 115 through the endplate opening 124, as shown in FIGS. 1 and 7. Additionally, or alternately the enhancing unit 140 may include a speaker 149 in data communication with an audio source (e.g., a mp3 player, radio, etc.), as shown in FIGS. 3a and 8.

Figure 3B:
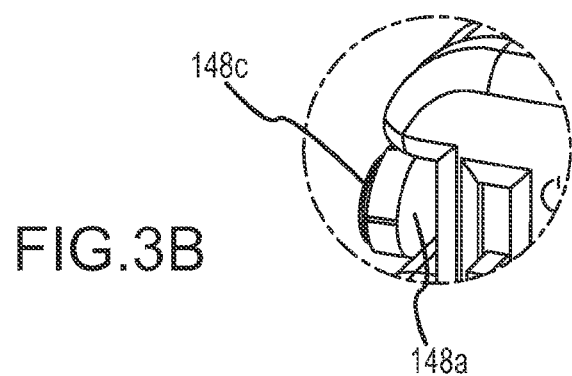

To maintain the enhancing unit 140 in the pocket 115 by selectively coupling the enhancing unit 140 to the endplate 120, the endplate 120 may define a catch 128 adjacent the opening 124 and the enhancing unit 140 may have a lock 148 complementary to the catch 128. As shown in FIG. 7, the catch 128 may be a recess 128a in the endplate 120. The lock 148 may include a spring tab 148a having a protrusion 148b and a grip portion 148c, as shown in FIGS. 3b and 4. The protrusion 148b is complementary to the recess 128a to selectively couple the enhancing unit 140 to the endplate through interaction between the protrusion 148b and the recess 128a. The grip portion 148c is accessible when the protrusion 148b interacts with the recess 128a (FIGS. 1 and 7) to selectively separate the protrusion 148b from the recess 128a. It may be preferable for the spring tab 148a to be biased to cause the protrusion 148b to interact with the recess 128a.

In use, the outer shell 110, endplate 120, and fill material 130 may be heated (e.g., in a microwave) or cooled (e.g., in a freezer). As the enhancing unit 140 is generally not microwavable or refrigeratable, the enhancing unit 140 may be removed from the pocket 115 (i.e., by separating the protrusion 148b from the recess 128a) prior to heating or cooling and then reattached after heating or cooling. After the fill material 130 is the desired temperature, the therapeutic device 100 may be used to heat or cool a body part (e.g., a sore muscle), and the enhancing unit 140 may be used to vibrate the fill material 130 (and therefore provide vibration to the user), provide audio, provide light, etc. The human hand configuration of the outer shell 110 may provide a convenient configuration for targeting various body parts.

It is understood that while certain forms of this invention have been illustrated and described, it is not limited thereto except insofar as such limitations are included in the following claims and allowable functional equivalents thereof.

The invention claimed is:

1. A therapeutic device, comprising:
   an outer shell configured as a three-dimensional human hand having a finger end and a wrist end and the outer shell defining an interior area, wherein the wrist end of the outer shell comprises an open end and the finger end of the outer shell comprises a closed end;
   an inner wall disposed within the interior area of the outer shell;
   a pocket in the interior area, wherein the pocket is defined by the inner wall, wherein the pocket has a closed end and an open end, wherein the pocket open end is positioned proximate the outer shell open end;
   an endplate coupled to the outer shell open end and coupled to the pocket open end to define a closed area between the endplate, the outer shell, and the inner wall, wherein the outer shell, the inner wall, and the endplate are impermeable, and wherein the end plate comprises an opening to allow access to the pocket;
   a fill material disposed in the closed area, wherein the fill material is configured to be at least one of heated and cooled to a desired temperature for providing a therapeutic effect;
   a vibrating unit disposed in the pocket, positioned proximate the end plate, and configured to vibrate the therapeutic device to provide a tactile effect; and
   wherein the therapeutic device emulates a human hand.

2. The device of claim 1, wherein the outer shell, the inner wall, the endplate, and the fill material are constructed of microwave safe materials.

3. The device of claim 1, wherein the fill material is configured to maintain the desired temperature for an extended period of time.

4. The device of claim 1, wherein the vibrating unit comprises a vibrating motor in electrical communication with a power source and a switch, and wherein the switch is accessible through the opening when the vibrating unit is disposed in the pocket.

5. A therapeutic device, comprising:
   an outer shell configured as a three-dimensional human hand and defining an interior area, wherein the outer shell has a wrist end opposite a finger end and the wrist end is positioned proximate an open end of the outer shell, and wherein the outer shell is constructed of a material that is heatable;
   an inner wall disposed within the interior area of the outer shell, wherein the inner wall is separated from the outer shell by a space;
   a pocket in the interior area, wherein the pocket is at least partially defined by the inner wall, wherein the pocket has a closed end and an open end, wherein the pocket open end is positioned proximate the outer shell open end;
   an endplate proximate to the outer shell open end and to the pocket open end to define a closed area between the endplate, the outer shell, and the inner wall, wherein the end plate is constructed of a material that is heatable;
   a heat-conductive fill material in the closed area, wherein the fill material is heatable to provide therapeutic heat, and wherein the inner wall is positioned between the pocket and the fill material to keep the heat from the fill material away of the pocket;
   an enhancing unit positioned within the pocket and removable through the wrist end, the enhancing unit comprising a vibrating motor and a power source, wherein the vibrating motor is configured to vibrate at least one of the fill material and the outer shell; and
   wherein the therapeutic device emulates a human hand.

6. The device of claim 5, further comprising a heating element to heat the device.

7. The device of claim 5, wherein the outer shell, the inner wall, and the endplate are impermeable.

8. The device of claim 1, wherein the endplate comprises a recess adjacent the opening, the vibrating unit comprises a protrusion complementary to the recess to selectively couple the vibrating unit to the endplate, and the vibrating unit comprises a grip portion accessible when the protrusion interacts with the recess to selectively separate the protrusion from the recess.

9. The device of claim 5, wherein the fill material is gel.
10. The device of claim 5, wherein the fill material is metal.
11. The device of claim 1, wherein the fill material is metal.

\* \* \* \* \*